(12) United States Patent
Chen

(10) Patent No.: US 6,392,409 B1
(45) Date of Patent: May 21, 2002

(54) DETERMINATION OF $T_1$ RELAXATION TIME FROM MULTIPLE WAIT TIME NMR LOGS ACQUIRED IN THE SAME OR DIFFERENT LOGGING PASSES

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/483,336

(22) Filed: Jan. 14, 2000

(51) Int. Cl.$^7$ ................................................. G01V 3/00
(52) U.S. Cl. ........................................ 324/303; 324/300
(58) Field of Search ................................ 324/303, 300, 324/307, 309, 318

(56) References Cited

U.S. PATENT DOCUMENTS

| | | | |
|---|---|---|---|
| 4,443,760 A | 4/1984 | Edelstein et al. | 324/309 |
| 5,486,762 A | 1/1996 | Freedman et al. | 324/303 |
| 5,936,405 A | 8/1999 | Prammer et al. | 324/303 |
| 6,097,184 A | 8/2000 | Flaum | 324/303 |

FOREIGN PATENT DOCUMENTS

GB    2343256 A    5/2000

OTHER PUBLICATIONS

A. Sezginer et al., An NMR High–Resolution Permeability Indiicator, SPWLA 40th Annual Loggind Symposium, May 30–Jun. 3, 1999, pp. 1–12.

Primary Examiner—Jay Patidar
Assistant Examiner—Brij B. Shrivastav
(74) Attorney, Agent, or Firm—Madan, Mossman & Sriram, P.C.

(57) ABSTRACT

Nuclear magnetic resonance measurements of a porous medium using multiple wait times are used for determining the longitudinal relaxation time $T_1$ time of oil in a hydrocarbon reservoir. The $T_1$ values of water in the formation are represented by a distribution. In a dual wait time implementation of the method, data are acquired with a short wait time TWS chosen such that the wetting fluid phase (e.g., brine) is completely relaxed but the hydrocarbon phase is partially relaxed, giving a sequence ECHOA and with a long wait time TWL giving an echo sequence ECHOB. Using known methods, the $T_2$ for the oil and water may be determined. The individual echo trains are summed and the $T_1$ values determined from the summed echo trains and the determined values of $T_2$. The summation greatly improves the SNR. An equivalent method determines the $T_1$ values by summation of a first echo train that is the sum of the individual echo trains and the summation of a second echo train that is the difference of the individual echo trains. The various summed values may also be used as for quality control of the data.

23 Claims, 8 Drawing Sheets

US 6,392,409 B1

DETERMINATION OF $T_1$ RELAXATION TIME FROM MULTIPLE WAIT TIME NMR LOGS ACQUIRED IN THE SAME OR DIFFERENT LOGGING PASSES

FIELD OF THE INVENTION

The invention is in the field of determination of petrophysical properties, including oil saturation, of medium using data from a Nuclear Magnetic Resonance (NMR) tool.

BACKGROUND OF THE INVENTION

A variety of techniques have been utilized in determining the presence and in estimating quantities of hydrocarbons (oil and gas) in earth formations. These methods are designed to determine formation parameters, including among other things, porosity, fluid content, and permeability of the rock formation surrounding the wellbore drilled for recovering hydrocarbons. Typically, the tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD"). Measurements have also been made when tripping a drillstring out of a wellbore: this is called measurement-while-tripping ("MWT").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating field $B_1$ in a direction perpendicular to $B_0$. This oscillating field is usually applied in the form of short duration pulses. The purpose of the $B_0$ field is to polarize the magnetic moments of nuclei parallel to the static field and the purpose of the $B_1$ field is to rotate the magnetic moments by an angle θ controlled by the width $t_p$ and the amplitude $B_1$ of the oscillating pulse. With the variation of the number of pulses, pulse duration, and pulse intervals, various pulse sequences can be designed to manipulate the magnetic moment, so that different aspects of the NMR properties can be obtained. For NMR logging, the most common sequence is the Carr-Purcell-Meiboom-Gill ("CPMG") sequence that can be expressed as $$TW-90-(t-180-t-echo)_n$$

After being tipped by 90°, the magnetic moment precesses around the static field at a particular frequency known as the Larmor frequency $\omega_0$, given by $\omega_0 = \gamma B_0$, where $B_0$ is the field strength of the static magnetic field and γ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals.

U.S. Pat. No. 5,023,551 issued to Kleinberg discloses an NMR pulse sequence that has an NMR pulse sequence for use in the borehole environment which combines a modified inversion recovery (FIR) pulse sequence with a series of more than two, and typically hundreds, of CPMG pulses according to $$[W_i-180-TW_i-90-(t-180-t-echo)_j]_i$$

where j=1,2, . . . J and J is the number of echoes collected in a single Carr-Purcell-Meiboom-Gill (CPMG) sequence, where i=1, . . . I and I is the number of waiting times used in the pulse sequence, where $W_i$ are the recovery times, $TW_i$ are the wait times before a CPMG sequence, and where t is the spacing between the alternating 180° pulses and the echo signals. Although a conceptually valid approach for obtaining $T_1$ information, this method is extremely difficult to implement in wireline, MWD, LWD or MWT applications because of the long wait time that is required to acquire data with the different TWs.

Proton NMR measurement is typically performed for well logging applications since hydrogen is abundant in reservoir fluids. T2 is very short in solids, but relatively long in liquids and gases, so that the proton NMR signal from the solid rock decays quickly and only the signal from fluids in the rock pores in the region of interest is seen. This signal may arise from hydrogen in hydrocarbon or water within the pores of the formation. The local environment of the hydrogen influences the measured T2 or "spin-spin" relaxation. For example, capillary bound fluid has a shorter T2 than fluid in the center of a pore, the so-called "free fluid." In this way, the NMR tool can be used advantageously to distinguish between producible fluid and non-producible fluid.

The NMR echo signals provide information about fluid and rock properties. Depending upon the goal of the investigation, various NMR measurement techniques can be used to obtain different petrophysical properties (e.g., partial and total porosities) or to discern multiphase fluids for hydrocarbon typing purposes. The different NMR acquisition techniques are characterized by differences in pulse timing sequences as well as repetition times between measurements. In addition, in wireline applications, multiple runs of NMR acquisition sequences with different parameters can be combined to enhance the analysis of the desired petrophysical information. However, in measurement-while-drilling applications or in measurement-while-tripping applications, it is not possible to make multiple runs, so that all the desired information must be obtained at one time while the borehole is being drilled or tripped.

The longitudinal relaxation time, $T_1$, of oil phase carries important petrophysical information that is critical to hydrocarbon volumetrics, viscosity, and hydrocarbon typing analysis from NMR logs. The ratio of $T_1/T_2$ is a potentially useful information revealing in-situ reservoir fluid characteristics. While $T_2$ can be estimated relatively easily, the estimation of $T_1$ is challenging particularly when reservoir fluids contain more than one fluid, e.g., oil and water, or gas and water system.

Several methods to identify and quantify hydrocarbon reservoirs have been employed during the last few years utilizing the effect of different wait times on the measured NMR signal. Depending upon the fluid properties, the wait time (TW) determines the amount of the polarization that contributes to the measured signal. For example, Akkurt et.al. disclose a Differential Spectrum Method (DSM) based upon this effect in their paper "NMR Logging of Natural Gas Reservoirs" presented at the 36$^{th}$ Annual Meeting of the Society of Professional and Well Log Analysts (SPWLA) in 1995. This approach takes advantage of the $T_1$ difference between hydrocarbons and water at reservoir conditions, and the short wait time (TWS) is chosen such that the fast relaxing water components are approximately fully polarized while the hydrocarbon components are not fully polarized. On the other hand, the long wait time (TWL) is typically chosen such that the hydrocarbon component is also nearly fully polarized. However, logging speed and overall signal to noise ratio (SNR) often dictates the selection of TWL to be less than optimal. Further, the TWL selected prior to acquisition may not be sufficiently long if the oil is lighter than expected. The $T_1$ information is critical to correct the polarization effect after the log is acquired.

Analysis of dual wait time data for $T_1$ estimation remains a particularly challenging task. In the prior art, a critical first step in the data analysis is to subtract the short wait time (TWS) echo data (ECHOB) from the long wait time echo data (ECHOA) in the time domain. Thus, practically, it requires that the two echo trains are at the exact same depth and have the same vertical sampling rate. This requirement makes it difficult to process multiple wait time echo trains acquired in different passes having different sampling rates, because of the cumbersome work involved in interpolating the two-dimensional echo matrices (typically, 500 elements per sample).

The poor signal to noise ratio (SNR) involved in the $T_1$ analysis is another major difficulty in the prior art. The situation is worsened by the subtraction of ECHOB from ECHOA because the noise level increases while the signal strength decreased in the resultant differential data.

There is a need for a method of obtaining $T_1$ information from multiple wait time data that provides stable estimates and does not suffer from very poor signal-to-noise ratio. Such a method should preferably be able to easily process data acquired with different logging passes with the same or different sampling rates without requiring the cumbersome work involved in interpolating two-dimensional echo matrices. The present invention satisfies this need.

SUMMARY OF THE INVENTION

The present invention is a method for acquiring nuclear magnetic resonance measurements of a porous medium using multiple wait times for determining the $T_1$ relaxation time of oil in a hydrocarbon reservoir. The $T_1$ values of water in the formation are represented by a distribution. In a dual wait time implementation of the method, data are acquired with a short wait time TWS chosen such that the wetting fluid phase (e.g., brine) is completely (or nearly completely) relaxed but the hydrocarbon phase is partially relaxed, giving a sequence ECHOA and with a long wait time TWL giving an echo sequence ECHOB. The individual echo trains are summed and the $T_1$ values determined from the summed echo trains. The summation greatly improves the SNR and gives a significant improvement in the stability of $T_1$ estimates. An equivalent method determines $T_1$ values derived from the summation of the sum and difference of the individual echo trains respectively. The various summed values may also be used as for quality control of the data.

DESCRIPTION OF THE PREFERRED EMBODIMENT

Figure 1:
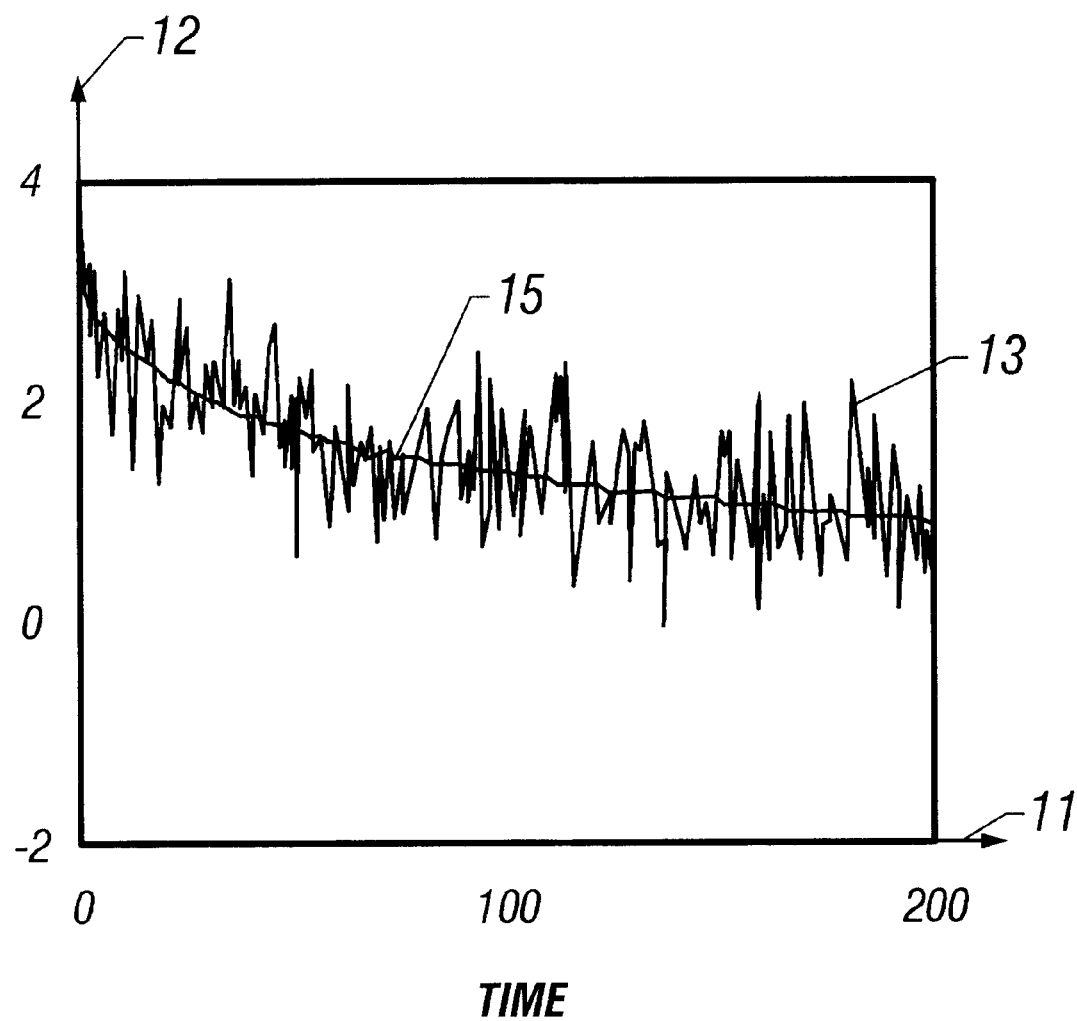
FIG. 1 is an example of an NMR echo train.

A typical nuclear magnetic resonance ("NMR") instrument which can make measurements according to this invention is described, for example, in U.S. Pat. No. 5,585,720 issued to Edwards, the contents of which are fully incorporated herein by reference. The instrument described in the Edwards '720 patent includes a permanent magnet for inducing a static magnetic field within the medium to be analyzed. In particular, the medium to be analyzed can include earth formations in the vicinity of a wellbore. The instrument in the Edwards '720 patent includes an antenna coil which can be wound around the magnet, circuitry for applying pulses of radio-frequency (RF) power to the antenna coil, and circuitry for detecting voltages induced in the antenna coil as a result of nuclear magnetic resonance phenomena, particularly that of hydrogen nuclei present in the earth formations.

As is known in the art, the RF pulses applied to the antenna coil of NMR apparatus such as the one in the Edwards '720 patent typically include an initial RF pulse having a duration and amplitude which reorients the nuclear spin axes of the hydrogen nuclei in the earth formations so that they become substantially perpendicular to the direction of the static magnetic field induced by the magnet. This first RF pulse induces rotation of about 90 degrees in the spin axes of the hydrogen nuclei. Later in the measurement cycle known in the art, a sequence of additional RF pulses (referred to as "refocusing pulses"), each having a duration and amplitude selected to reorient the extant nuclear spin axes by 180 degrees, is applied to the antenna coil. In between refocusing pulses, the antenna coil is connected to a receiver circuit to detect voltages induced in the antenna coil as the nuclear spin axes "rephase", an event called the pulse-echo or spin echo. The combination of the tipping pulses and refocusing pulses is known as a Carr-Purcell-Meiboom-Gill (CPMG) sequence. As is understood by those skilled in the art, the amplitude of the induced voltages from spin rephasing (pulse-echo voltages) decreases after each successive refocusing pulse applied to the antenna coil. The rate at which the amplitude of the successive pulse-echo voltages decays is related to properties of the earth formations such as the fractional volume of pore space and the type of fluids filling the pore space, as is known in the art.

In co-pending U.S. application Ser. No. 09/151,871, having the same assignee as the present application and the contents of which are incorporated herein by reference, it has been disclosed that the refocusing pulses should preferably have a duration and amplitude selected to cause the nuclear spin axes to reorient by an angular deflection different from 180 degrees, and between 100° and 135°. With such a refocusing pulse, the power requirements are reduced and the signal to noise ratio of the echos is improved.

Accordingly, the RF field of the present invention includes a pulse sequence $$TW-90_{\pm X}-(t-X-t-echo)_j \quad (1)$$

where TW is a wait time, $90_{\pm X}$ represent phase-alternated tipping pulses for tipping the nuclear spins at an angle substantially equal to ninety degrees to cause precession thereof, t is the spacing between the alternating refocusing pulse and the echo signal, X is an optimized refocusing pulse, and j=1, 2, . . . J, where J is the number of echoes collected in a single sequence of pulses.

The present invention is a method for evaluating the petrophysical properties of a reservoir including an oil and a water. For exemplary purposes, the invention is illustrated by using data acquired with two different wait times TWS and TWL in equation (1). For such an example, the echo trains may be represented as $$ECHOB(j) = \sum_k \left\{ \phi_{k,water} HI_{water} \exp\left(-\frac{jTE}{T_{2k,water}}\right)(1-\alpha_{k,SW}) \right\} + \quad (2)$$

$$\phi_{oil} HI_{oil} \exp\left(-\frac{jTE}{T_{2oil}}\right)(1-\alpha_{SO})$$

$$ECHOA(j) = \sum_k \left\{ \phi_{k,water} HI_{water} \exp\left(-\frac{jTE}{T_{2k,water}}\right)(1-\alpha_{k,LW}) \right\} + \quad (3)$$

$$\phi_{oil} HI_{oil} \exp\left(-\frac{jTE}{T_{2oil}}\right)(1-\alpha_{LO})$$

FIG. 1 shows a typical example of a noisy echo train 13. The abscissa 11 is the time in milliseconds and the ordinate 13 is the amplitude. In the simplest case where the index k has a single value, equations (2) and (3) depict a curve that is the sum of two exponentials: at time zero (j=0) the value is related to the water saturated porosity $\phi_{water}$ and the oil saturated porosity $\phi_{oil}$. The decay rate for the exponentials is related to the $T_2$ of the respective components. In this simple case, the determination of $T_2$ reduces to the problem of curve-fitting a smooth curve 15 that is the sum of two exponentials to the data 13. In the general case, due to surface relaxation effects, the water may have some unknown distribution that is analytically represented by a plurality of values of the index k.

In equations (2) and (3), the following notation has been used:

$$\alpha_{SO}=\exp(-TWS/T_{1oil}), \alpha_{LO}=\exp(-TWL/T_{1oil})$$

$$\alpha_{k,SW}=\exp(-TWS/T_{1k,water}) \text{ and } \alpha_{1k,LW}=\exp(-TWL/T_{k,water}).$$

The terms HI refer to the hydrogen index.

In the present invention, the water phase is substantially fully polarized by both the TWS and TWL waiting periods. Under those conditions, equations (2) and (3) become:

$$ECHOB(j) \approx \sum_k \left\{ \phi_{k,water} HI_{water} \exp\left(-\frac{jTE}{T_{2k,water}}\right) \right\} + \quad (4)$$

$$\phi_{oil} HI_{oil} \exp\left(-\frac{jTE}{T_{2oil}}\right)(1-\alpha_{SO})$$

and $$ECHOA(j) \approx \sum_k \left\{ \phi_{k,water} HI_{water} \exp\left(-\frac{jTE}{T_{2k,water}}\right) \right\} + \quad (5)$$

$$\phi_{oil} HI_{oil} \exp\left(-\frac{jTE}{T_{2oil}}\right)(1-\alpha_{LO})$$

The oil phase is depicted by a single value of $T_1$ and $T_2$ while the values of $T_1$ and $T_2$ for the water are indexed by k to denote several components because of the effect of surface relaxation and the pore-size distribution on the wetting phase. In equations (2)–(5), TE is the interecho spacing.

An equivalent distribution may be defined in terms of the echo difference and the echo average signals:

$$ECDF(j)=ECHOA(j)-ECHOB(j) \quad (6)$$

and $$ECAV(j)=(ECHOA(j)+ECHOB(j))/2 \quad (7)$$

as $$ECDF(j) \approx \phi_{oil} HI_{oil} \exp\left(-\frac{jTE}{T_{2oil}}\right)(\alpha_{SO}-\alpha_{LO}) \quad (8)$$

and $$ECAV(j) = \sum_k \left\{ \phi_{k,water} HI_{water} \exp\left(-\frac{jTE}{T_{2k,water}}\right) \right\} + \quad (9)$$

$$\phi_{oil} HI_{oil} \exp\left(-\frac{jTE}{T_{2oil}}\right)\left(1-\frac{\alpha_{SO}+\alpha_{LO}}{2}\right)$$

In equations (2)–(9), the sample index has been omitted. It is understood that all the echo trains defined above are sample-indexed.

The equally time-spaced echo trains described in equations (4), (5), (8), and (9) form a geometric series with a factor of $\exp(-TE/T_2)$. Summation over the echo time j of equation (4), and using the summation rule of a geometric series gives $$\sum_j ECHOA(j) = \sum_k \frac{\phi_{k,water} HI_{water}}{\exp\left(\frac{TE}{T_{2k,water}}\right)-1} + \quad (10)$$

$$\phi_{oil} HI_{oil}(1-\alpha_{LO}) \frac{1-\exp\left(-\frac{N \cdot TE}{T_{2oil}}\right)}{\exp\left(\frac{TE}{T_{2oil}}\right)-1}$$

$$= \sum W + \phi_{oil} HI_{oil}(1-\alpha_{LO}) \sum H$$

where $$\sum W \equiv \sum \frac{\phi_{k,water} HI_{water}}{\exp\left(\frac{TE}{T_{2k,water}}\right)-1} \text{ and} \quad (11)$$

$$\sum H \equiv \frac{1 - \exp\left(\frac{N \cdot TE}{T_{2oil}}\right)}{\exp\left(\frac{TE}{T_{2oil}}\right) - 1} \quad (12)$$

are used for notational simplification. Another simplification that can be made is that $$\sum W \equiv \sum_k \frac{\phi_{k,water} HI_{water}}{\exp\left(\frac{TE}{T_{2k,water}}\right) - 1} \quad (13)$$

$$\approx \sum \frac{\phi_{k,water} HI_{water} T_{2k,water}}{TE\left(1 + \frac{TE}{2T_{2k,water}}\right)}$$

because the number of echoes typically acquired in NMR logging is sufficiently large that N·TE is much greater than the longest water $T_2$ component. Furthermore, if the shortest water $T_2$ component is limited to, say, 4 ms., then equation (1) simplifies to $$\exp\left(-\frac{N \cdot TE}{T_{2k,water}}\right) = 0 \quad (14)$$

The simplification of equations (13) and (14) form an optional embodiment of the invention. The invention, as described further, may be practiced, with or without these simplifications.

Similarly, summation of equation (5) gives $$\sum_j ECHOB(j) = \sum W + \phi_{oil} HI_{oil}(1 - \alpha_{SO}) \sum H, \quad (15)$$

summation of (8) gives $$\sum_j ECDF(j) = \phi_{ol} HI_{ol} \cdot (\alpha_{SO} - \alpha_{LO}) \sum H \quad (16)$$

while summation of (9) gives $$\sum_j ECAV(j) = \sum W + \phi_{oil} HI_{oil}\left(1 - \frac{\alpha_{SO} + \alpha_{LO}}{2}\right) \cdot \sum H \quad (17)$$

There are three alternative methods in which the longitudinal relaxation time $T_1$ are determined in the present invention. One method uses equations (10) and (15) and relies on the determination of the quantity $$R_\alpha = \frac{\sum ECHOA - \sum W}{\sum ECHOB - \sum W} = \frac{1 - \alpha_{LO}}{1 - \alpha_{SO}}. \quad (18)$$

A second method uses equations (16) and (17) and the determination of the quantity $$R_b = \frac{\sum ECAV - \sum W}{\sum ECDF} = \frac{1 - \frac{\alpha_{SO} + \alpha_{LO}}{2}}{\alpha_{SO} - \alpha_{LO}} \quad (19)$$

and a third method uses equation (17) and the determination of the quantity $$R_c = \frac{\sum ECDF}{VO \cdot \sum H} = \frac{(\alpha_{SO} - \alpha_{LO})}{(1 - \alpha_{LO})}. \quad (20)$$

where $VO = \phi_{oil} HI_{oil}(1 - \alpha_{LO})$ can be estimated from the $T_2$ spectra of the TWL echo data. VO is the total oil signal computed from oil $T_2$ bins whereas $\Sigma H$ is defined in equation (14). The methods require the evaluation of $\Sigma W$ from equation (14) and $\Sigma H$ from equation (12). In equation (14), $\phi_{k,water}$ and $T_{2k,water}$ are the partial porosity and corresponding $T_2$ values of the water components from the corresponding $T_2$ spectra. As would be known to those versed in the art, these include $T_2$ components below some value $T_{2cutoff}$. The water hydrogen index is usually very close to unity. Hence $\Sigma W$ is fully determined from the $T_2$ spectra.

In actual practice, ECHOA and ECHOB data can yield slightly different values of $\Sigma W$. Accordingly, in a preferred mode of the invention, $\Sigma W$ is determined from ECAV data.

In one embodiment of the invention, the ECHOA and ECHOB data are obtained in different logging passes. In this case, $\Sigma W$ is determined separately for each logging pass and then averaged.

If equation (20) is to be used, then the quantity $\phi_{oil} HI_{oil}(1 - \alpha_{LO})$, denoted hereafter by VO, needs to be evaluated. This too is determined from the $T_2$ spectra of the TWL data.

$$\sum H \equiv \frac{1 - \exp\left(\frac{N \cdot TE}{T_{2oil}}\right)}{\exp\left(\frac{TE}{T_{2oil}}\right) - 1} \approx \frac{T_{2oil}}{TE} \cdot \left[1 - \exp\left(-\frac{N \cdot TE}{T_{2oil}}\right)\right]$$

requires knowledge of $T_{2oil}$. In a preferred embodiment of the invention, this is approximated by the geometric means of the oil bins in the $T_2$ spectra.

As noted above, one embodiment of the invention is based upon a solution of equation (18). Returning now to equation (18) and using the definition of $\alpha_{SO}$, $$T_{1oil} = \frac{-TWS}{\ln\left(1 - \frac{1 - \alpha_{LO}}{R_a}\right)} \quad (21)$$

There is more than one way to solve this equation. In a preferred embodiment of the invention, an approximate solution is first determined by setting $\alpha_{LO}$ equal to zero, which is equivalent to assuming that TWL>$3T_{1oil}$. With this approximation, the initial estimate of $T_{1oil}$ is $$T_{1oil}|_{1st} = \frac{-TWS}{\ln(R_a - 1) - \ln(R_a)} \quad (22)$$

If the value given by equation (22) is less than TWL/3, no iteration is needed. If the value given by equation (22) is greater than TWL/3, then the estimated value from equation (22) is used to find a first approximation of $\alpha_{LO}$ that is then inserted into equation (21) and the value of $T_{1oil}$ is determined again. This iterative process is continued until $$\left|\frac{T_{1oil,k} - T_{1oil,k-1}}{T_{1oil,k}}\right| \leq \varepsilon \quad (23)$$

where $\varepsilon$ is a user specified tolerance.

As noted above, a second embodiment of the invention is based upon a solution of equation (19). Using equation (19)

and the definition of $\alpha_{sO}$ gives $$T_{1oil} = \frac{-TWS}{\ln\left(\frac{2 + \alpha_{LO}(2R_b - 1)}{2R_b + 1}\right)} \quad (24)$$

A first approximation to the solution is obtained by setting $\alpha_{LO}=0$, giving $$T_{1oil}|_{1st} = \frac{-TWS}{\ln 2 - \ln(2R_b + 1)}. \quad (25)$$

Additional iterations are carried out as described above with reference to the solution of equation (18).

As noted above, a third embodiment of the invention is based upon a solution of equation (20). Using equation (19) and the definition of $\alpha_{sO}$ gives $$T_{oil} = -\frac{TWS}{\ln\left[\frac{(1 - \alpha_{LO}) \cdot R_c}{\Sigma H} + \alpha_{LO}\right]} \quad (26)$$

The first order approximation with $\alpha_{LO}=0$ gives $$T_{1oil}|_{1st} = -\frac{TWS}{\ln\left[\frac{R_C}{\Sigma H}\right]} \quad (27)$$

with additional iterations carried out as described above.

Figure 2:
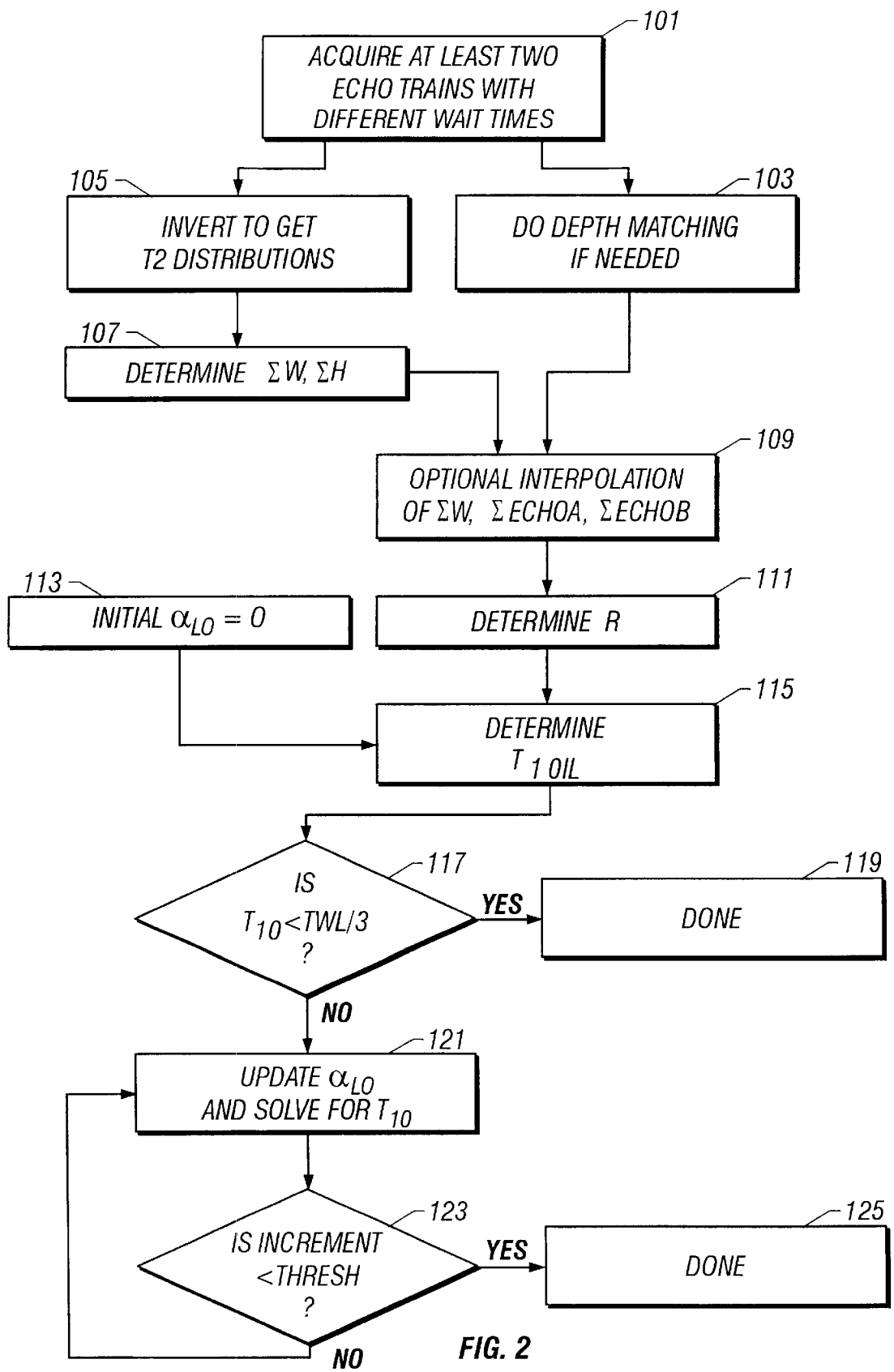
FIG. 2 is a flow chart illustrating one embodiment of the present invention for determining the longitudinal relaxation time $T_1$ of a formation.

Turning now to FIG. 2, a flow chart of the principal steps for the determination of the $T_{1oil}$ are shown. Beginning at 101 at least two sets of NMR echo trains are acquired with different wait times of an RF pulse sequence such as given by equation (1). In a dual wait time implementation of the method, data are acquired with a short wait time TWS chosen such that the wetting fluid phase (e.g., brine) is completely relaxed but the hydrocarbon phase is partially relaxed, giving a sequence ECHOB and with a long wait time TWL giving an echo sequence ECHOA. These echo trains may be obtained in one or more passes.

If the multiple echo trains are not acquired in the same logging pass, a depth matching of the data is performed 103. This depth matching is preferably done using the sums of the echo trains (ΣECHOA and ΣECHOB in the dual wait time implementation). The sums of the echo trains are used for depth matching because of the improved signal-to-noise ratio (SNR) over the individual echo trains.

The echo train data are inverted to give the $T_2$ distributions of the oil and water using known techniques 105. From these $T_2$ distributions, the terms ΣW and ΣH are calculated 107 as needed, depending upon the method of determination of the $T_1$ of the oil, i.e., whether it is based upon a solution of equation (18), (19) or (20). As noted above, the choice of equations (18), (19) or (20) depends upon the particular combination of the summed trains ΣECHOA, ΣECHOB, ΣECAV and ΣECDF used for obtaining the $T_1$. These may be referred to as the first, second, third and fourth summed signals. If the individual data sets are not acquired with the same depth sampling interval, then ΣECHOA, ΣECHOB, ΣW and ΣH are interpolated and vertically resampled to give data with the same vertical sampling. Such methods for interpolation and resampling would be known to those versed in the art.

Depending upon the particular combination of the summed trains ΣECHOA, ΣECHOB, ΣECAV and ΣECDF used, a value of R corresponding to equation (18),(19) or (20) is determined. Based upon an initial estimate of $\alpha_{LO}=0$ at 113, an initial estimate of $T_{1oil}$ is obtained by solution of equation (22), (25) or (27). If this initial estimate is less than TWL/3 it is accepted 117, 119. If the difference is greater than TWL/3, the value of $\alpha_{LO}$ is updated and a new solution for $T_{1oil}$ is obtained 121 as described above. A check is made on the difference of two consecutive $T_{1oil}$ estimates 123 and if the difference is less than a predetermined threshold, the value of $T_{1oil}$ is accepted 125. If the difference at 123 is greater than the threshold, the values of $\alpha_{LO}$ and $T_{1oil}$ are iteratively updated.

It should be noted that the summation of the echo trains ECHOA and ECHOB and the determination of ECHOAV and ECHODIF are both linear operations that are commutative. Accordingly,

ΣECHOAV=(ΣECHOA+ΣECHOB)/2 and

ΣECHDIF=ΣECHOA−ΣECHOB

Hence the determination of ΣECHOAV and ΣECHDIF from ECHOAV and ECHODIF is completely equivalent to determining ΣECHOAV and ΣECHDIF from ΣECHOA ΣECHOB.

Another aspect of the invention is in the quality control of NMR logging. It is common practice in well logging to acquire a small depth interval of a log in repeated passes. For NMR logging, a satisfactory log must be repeatable for both the porosity and the characteristic $T_2$ decay of the echo trains.

Figure 3:
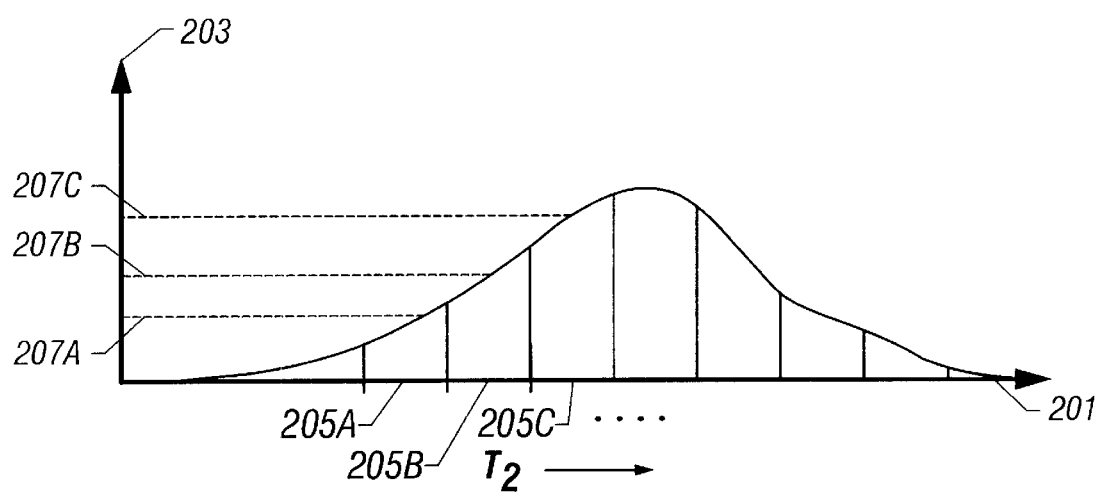
FIG. 3 illustrates an example of the variation in $T_2$ of a formation.

FIG. 3 is an illustration of a typical porosity—$T_2$ distribution. The abscissa 201 is the value of $T_2$ and the ordinate is the porosity of the formation having a particular value of $T_2$. Commonly, the $T_2$ axis is binned into $k_{max}$ regions 205a, 205b, 205c . . . and the associated partial porosity ppor is denoted by the values 207a, 207b, 207c . . . The total porosity of the formation is then given by $$\phi = \sum_{k=1}^{k_{max}} ppor(T_{2k}) \quad (28)$$

Prior art log verification procedures rely on obtaining a match between the total porosity obtained in different logging passes. Since the porosity distribution is determined from inversion of echo train data, the accuracy of ppor is subject to errors due to random noise and to inversion artifacts.

Using the sum of the echos in an echo train has a number of advantages over prior art methods. First, the sum-echo is responsive to one or both of variations of porosity and $T_2$. Secondly, the sum-echo does not require an inversion of the echo train, making it free of inversion artifacts. Thirdly, the sum-echo method has a larger SNR than the individual echos and is less affected by noise in the echo trains.

The same features of the sum-echo processing also make it possible to determine whether a multiple wait time set of data has adequate wait times.

Figure 4:
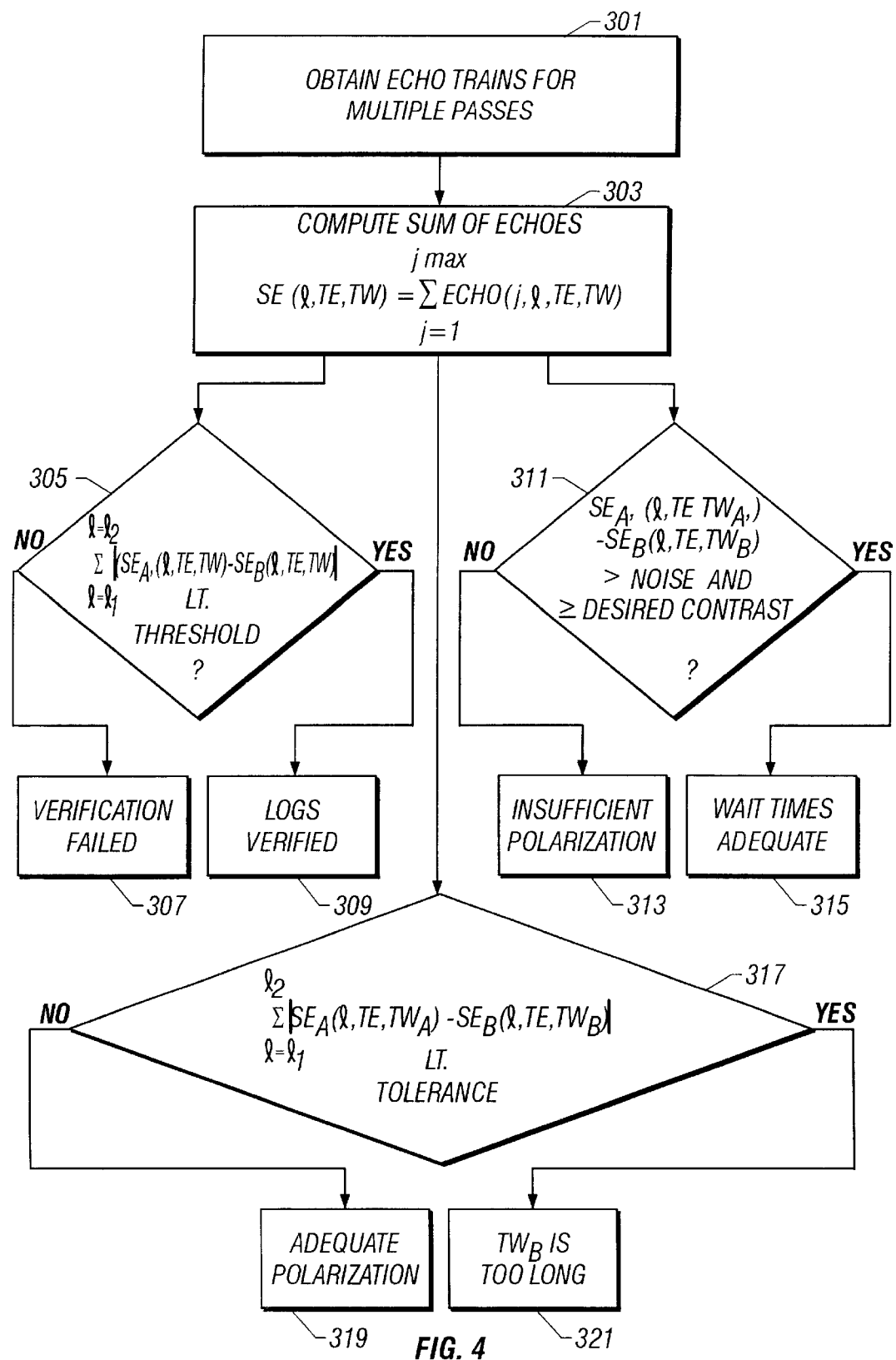
FIG. 4 is a flow chart illustrating an embodiment of the present invention for quality control of multiple sets of acquired data.

These aspects of the invention are illustrated in FIG. 4. Starting at 301, echo trains are obtained for multiple logging passes. These could be with either the same wait time, in which case, the objective is to check the quality of the logs, or could be with different wait times, in which case the objective is to check the adequacy of the wait times for use as discussed above.

At 303, the sum of the echo trains is computed for each echo train. The individual echo trains ECHO acquired at 301 are indexed in terms of j, the echo number, l, the depth, TE, the interecho time, and TW, the wait time. The sums of the echo are denoted by SE wherein the index j has been summed over a range of 1 to jmax.

One kind of quality check that may be done is to compare different logging passes and is shown at 305 where sums $SE_A(l, TE, TW)$ and $SE_B(l, TE, TW)$ of the two echo trains are compared. For this check, the wait times are the same for the two passes. An absolute difference between the two is determined for each depth l and a sum of the absolute differences is computed for a range of depths from $l=l_1$ to $l=l_2$. If this summed absolute difference is less than a predetermined threshold value, the logs are acceptable 309. If this summed difference exceeds a predetermined threshold, the logs are not verified 307 and are flagged for further review. Instead of performing this check over a range of depths, when $l_1=l_2$, a point by point verification may be made. In an optional embodiment of the invention, This verification of different logging passes may optionally be done when the check at 305 is performed in real time, i.e., while the second logging pass is being carried out. For this real-time implementation, the steps 301 and 303 for the first logging pass are performed ahead of time and the steps 301 and 303 for the second pass are performed while the logging is being carried out.

A second check that may be performed with the present invention is shown at 311 where a comparison is made between a sum $SE_A(l, TE, TW_A)$ of a first echo train acquired with a wait time $TW_A$ and a sum $SE_B(l, TE, TW_B)$ of a second echo train acquired with a wait time $TW_B$, where $TW_A>TW_B$. If this difference exceeds a first threshold based upon SNR considerations and exceeds a second threshold based upon a desired contrast in polarizations associated with the individual wait times, then the wait times have been chosen satisfactorily 315. If, however, the difference does not exceed the first and second thresholds, then there is insufficient contrast in the polarizations 313 produced by the two wait times. At this point, one of two options exist: the first is to reduce $TW_B$ while satisfying the requirement that the wait time be sufficient to substantially fully polarize the wetting phase (water) in the formation. The second alternative is to increase $TW_A$. The latter is possible only if the originally chosen $TW_A$ does not fully polarize all the signals.

A third check at 317 determines a gated sum over depths of the absolute difference between the sum $SE_A(l, TE, TW_A)$ of an echo train acquired with a wait time $TW_A$ and the sum $SE_B(l, TE, TW_B)$ of an echo train acquired with a wait time $TW_B$, where $TW_A>TW_B$. This check is applied in cases where the signal-to-noise ratio is poor or the difference signal is expected to be small, as in gas reservoirs. If the difference is too small, it is an indication 321 it is in indication that $TW_B$ is too long. If the difference is sufficiently large 319 then the wait times have been chose adequately.

Another aspect of the invention is the ability to identify changes in the region of examination during the acquisition of an echo train. During the acquisition of a complete echo train, any change in the sensitive volume after the application of the 90° tipping pulse results in an incorrectly rapid decay of the echo train, while the porosity determination is not affected. Changes in the sensitive volume may occur due to transverse vibration of the tool, particularly in MWD applications, or due to borehole rugosity. The problem is compounded in situations where the formation fluid has slow relaxation times. The problem is not easily detected by averaging data from multiple samples as it may vary from one depth to the next. In one embodiment of the invention, use is made of the sum of echo trains to identify depths at which data is of poor quality.

Figure 5:
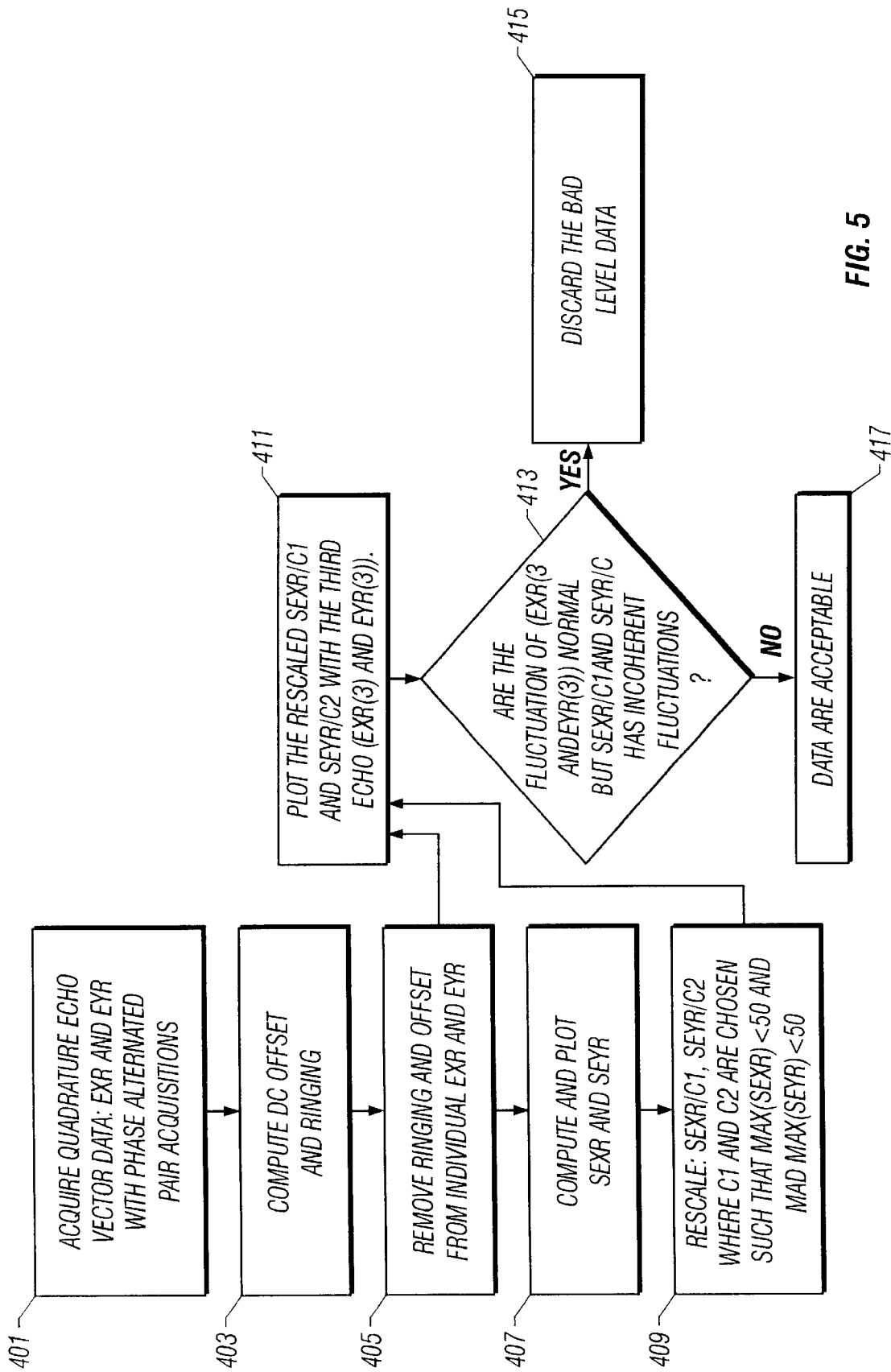
FIG. 5 is a flow chart illustrating an embodiment of the present invention for quality control of data acquired in a single logging pass.

This is illustrated in FIG. 5, where use is made of both the in-phase and quadrature components of the echo data. These are denoted by EXR and EYR 401. This is in contrast to conventional methods where the amplitude of the depth averaged vector sum of EXR and EYR is used in data analysis. The DC offset and the ringing are determined separately for the in-phase and quadrature component data 403. U.S. Pat. No. 4,443,760 to Edelstein gives an example of how the DC offset may be reduced using phase alternated RF pulses, i.e., on in which the polarity of the 90° tipping pulse is reversed from one pulse sequence to another. U.S. Pat. No. 5,712,566 to Taicher discloses methods for reducing the effect of magnetoacoustic and magnetostrictive ringing. The DC offset and the ringing are reduced EXR and EYR 405. The next step is the determination of SEXR and SEYR, the summed EXR and EYR echo trains 407, the summation being performed as described above. For convenience, SEXR and SEYR are separately normalized to a convenient scale, e.g., a maximum value of 50. A combined plot is then produced showing the scaled SEXR and SEYR as a function of depth along with EXR(3) and EYR(3), the third sample of the individual in-phase and quadrature echo trains 411. A comparison is made between the sum echo traces and the third echo 413. If the fluctuations of the third echo are normal while the fluctuations of the sum echos are not normal, the data at the depth where there is such a difference are unreliable 415. If, on the other hand, the data, the fluctuations of the third echo and the fluctuations of the sum echo are both normal, then the data at those depths is reliable.

Figure 6:
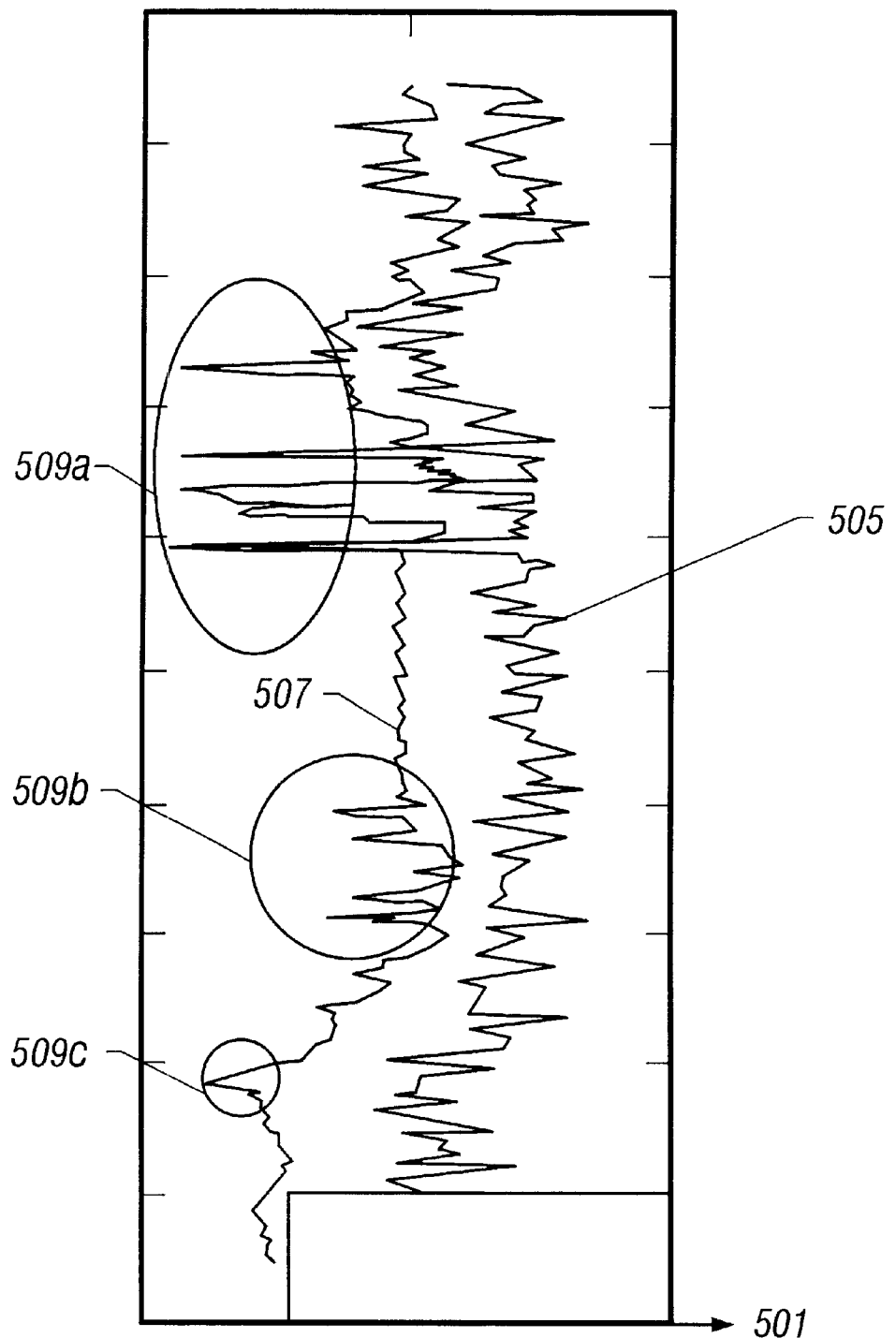
FIG. 6 shows an example of data that have been processed using the embodiment of FIG. 5.

FIG. 6 gives an illustrative example showing a comparison plot. The ordinate is the depth at which measurements are made by a logging instrument and abscissa is the NMR measurement. 505 is the log of quadrature component of the third echo EYR(3) as measured by the NMR instrument while 507 is the sum of the echos SEYR. The EYR(3) shows typical fluctuations that could be associated with porosity changes in the formation. There are depths, highlighted by 509a, 509b and 509c where the SEYR shows "spikes" that are indicative of abnormal decays of the echo trains. Data at these depths are suspect.

Figure 7:
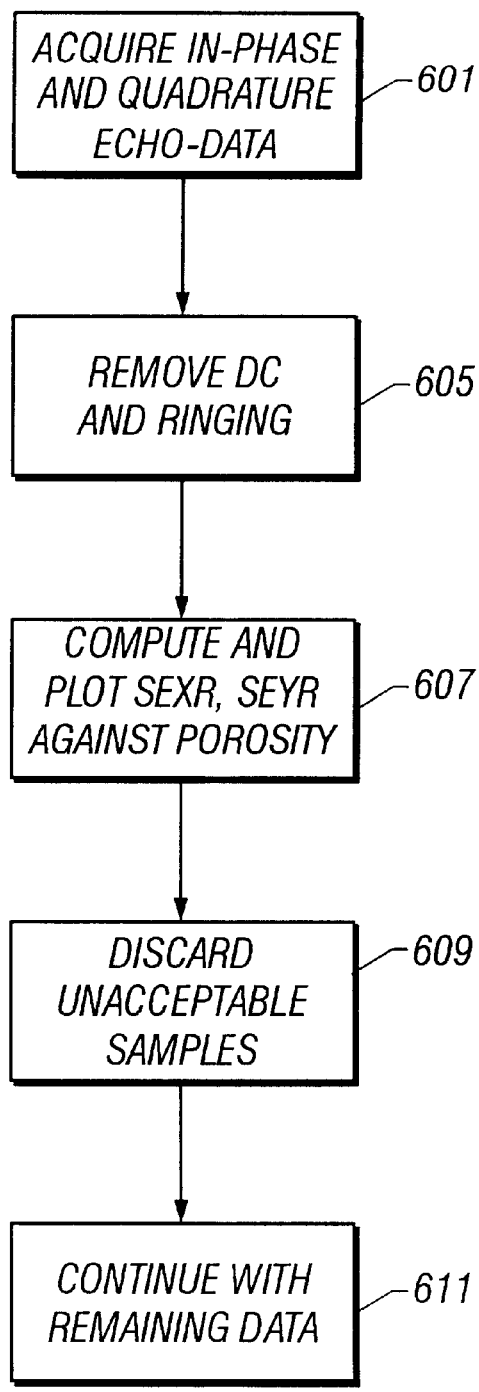
FIG. 7 is a flow chart illustrating an embodiment of the invention for quality control of data acquired in a formation where properties are expected to be substantially constant.
Figure 8:
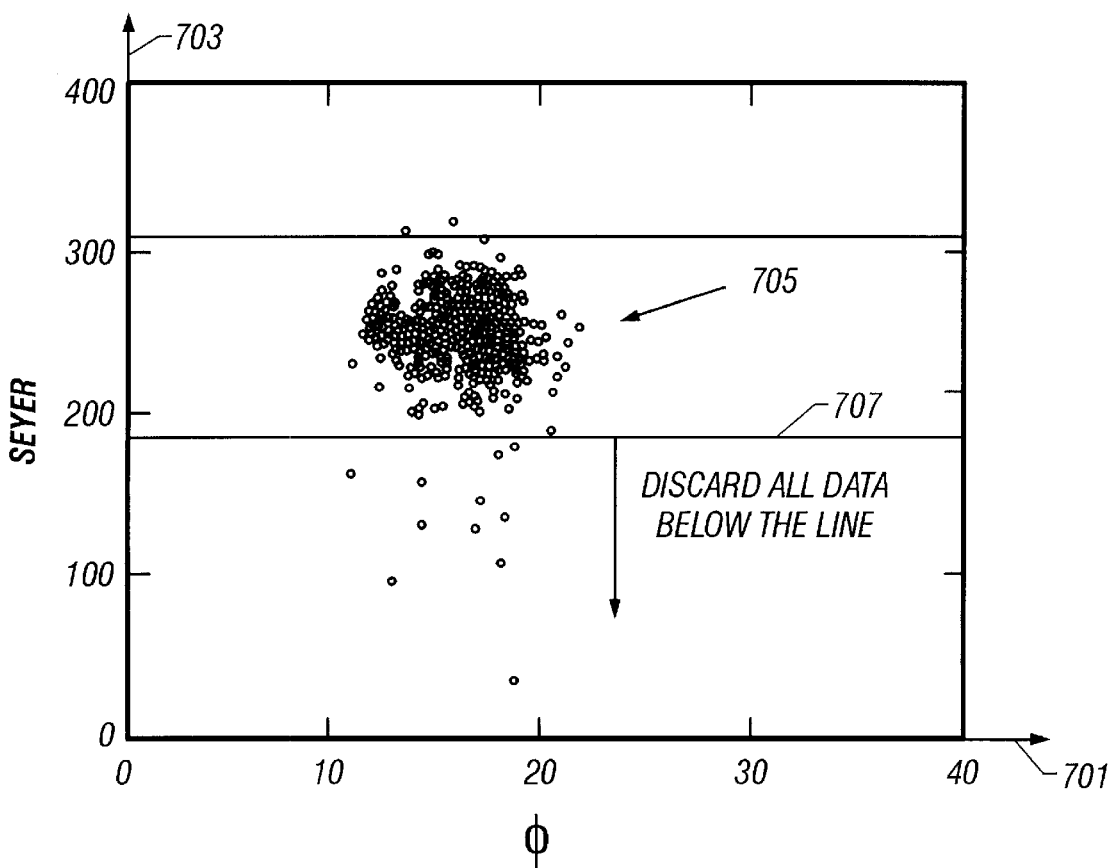
FIG. 8 illustrates the rejection of data points with abnormally short echo decay.

FIG. 7 illustrates another embodiment of the present invention for use in relatively homogenous intervals where based upon other log information (i.e., porosity), little variation in the NMR signals is expected. Such intervals are commonly associated with hydrocarbon reservoirs. In-phase and quadrature data are acquired 601 as discussed above and DC and ringing removed 605. The summed in-phase and quadrature signals SEXR and SEYR are determined 607. A cross-plot of porosity and either SEXR or SEYR is constructed for all data samples within the interval 607. An example of such a cross-plot is shown in FIG. 8 where the abscissa 701 is the porosity and the ordinate is the summed signal (SEXR or SEYR); in the example of FIG. 8, SEYR is plotted. Most of the data points form a reasonably well defined cluster 705 but there are several data points that are "outliers" as defined by a line such as 707. These samples have an abnormally short echo decay constant. As would be known to those versed in the art, electronics problems and abnormal tool movement during the echo train acquisition would cause just such an anomalously short echo decay. Accordingly, these outliers of abnormally low values of SEYR are discarded (609 in FIG. 7) and the remaining data points may be used for further processing and analysis 611.

The reason for using the third echo for such a comparison is that the first two echos typically exhibit large variations of the "ring down" of the instrument is not properly accounted for or suppressed. The third echo is less degraded by this and is consequently more stable.

Those skilled in the art will devise other embodiments of this invention which do not depart from the spirit of the invention as disclosed herein. Accordingly, the invention should be limited in scope only by the attached claims.

What is claimed is:

1. A method of determining a parameter of interest of a volume of earth formation in a reservoir adjacent a borehole, said parameter of interest including at least one of a longitudinal relaxation time $T_1$ and a transverse relaxation time $T_2$ of a fluid in the reservoir, the method comprising:
   (a) using a magnet assembly on a borehole tool conveyed in the borehole at at least one depth for producing a static magnetic field in said volume of the formation thereby aligning nuclear spins within said volume parallel to a direction of the static field;
   (b) producing a radio frequency (RF) magnetic field in said volume of the formation with an antenna on the borehole tool, said RF magnetic field having a direction orthogonal to a direction of the static field, the RF field including a first pulse sequence $TW_A$–90–(t–X–t–echo)$_j$ to produce a first echo train and at least one second pulse sequence $TW_B$–90–(t–X–t–echo)$_j$ to produce at least a second echo train,
      wherein 90 is a tipping pulse for tipping the nuclear spins at an angle substantially equal to ninety degrees to cause precession thereof, $TW_A$ is a first wait time, $TW_B$ is a second wait time, X is a refocusing pulse, and j=1, 2, . . . J, where J is the number of echoes collected in a single sequence of pulses;
   (c) measuring with the borehole tool the first and at least one second echo train;
   (d) determining at least one summed signal selected from the group of: (i) a sum of the first echo train, defining a first summation signal, (ii) a sum of the at least one second echo train, defining a second summation signal, (iii) a sum of an average of the first and at least one second echo train, defining a third summation signal, and, (iv) a sum of a difference of the first echo train and the at least one second echo train, giving a fourth summation signal; and
   (e) determining the parameter of interest from the at least one summed signal.

2. The method of claim 1 wherein $TW_A$ is different from $TW_B$.

3. The method of claim 2 wherein the parameter of interest comprises a longitudinal relaxation time $T_1$ of an oil in the reservoir.

4. The method of claim 3 wherein $TW_B$ is sufficiently long to polarize partially the oil in the formation and polarize substantially all of the water and wherein $TW_A$ is greater than $TW_B$.

5. The method of claim 4 wherein the at least one summed signal further comprises the fourth summation signal, and determining the parameter of interest further comprises using said fourth summation signal.

6. The method of claim 5 wherein the first and at least one second echo train are acquired in different passes of the logging tool and the at least one summed signal further comprises the first summation signal and the second summation signal, and determining the parameter of interest further comprises depth matching using the first and second summation signals.

7. The method of claim 4 wherein the at least one summed signal further comprises the first summation signal and the second summation signal, and determining the parameter of interest further comprises using said first and second summation signals.

8. The method of claim 1 wherein the first and at least one second echo train are acquired in different passes of the logging tool, and determining the parameter of interest further comprises depth matching using the first and second summation signals.

9. The method of claim 4 wherein the at least one summed signal further comprises the third summation signal and the fourth summation signal, and determining the parameters of interest further comprises using said third and fourth summation signals.

10. The method of claim 9 wherein the first and at least one second echo train are acquired in different passes of the logging tool and the at least one summed signal further comprises the first summation signal and the second summation signal, and determining the parameter of interest further comprises depth matching using the first and second summation signals.

11. The method of claim 3 wherein determining the parameter of interest further comprises determining a transverse relaxation time $T_2$ of the oil in the reservoir.

12. The method of claim 11 further comprising determination of a distribution of transverse relaxation times $T_2$ of water in the reservoir.

13. The method of claim 2 wherein the at least one depth further comprises a plurality of depths.

14. The method of claim 2 wherein the first pulse sequence and the second pulse sequence are applied in one or more logging passes.

15. The method of claim 1 wherein the refocusing pulse is an optimized refocusing pulse.

16. The method of claim 1 wherein the at least one summed signal further comprises the first summation signal and the second summation signal and wherein $TW_A$ is greater than $TW_B$, the method further comprising:
    (i) determining an absolute difference between the first and second summation signal at the at least one depth; and
    (ii) changing at least one of $TW_A$ and $TW_B$ if said absolute difference is less than a predetermined value.

17. The method of claim 16 wherein the at least one depth further comprises a plurality of depths, the method further comprising determining a sum of said absolute differences over the plurality of depths and changing at least one of $TW_A$ and $TW_B$ if said sum of absolute differences is less than a predetermined value.

18. The method of claim 1 wherein the at least one summed signal further comprises the first summation signal and the second summation signal, wherein $TW_A$ is equal to $TW_B$ and the first and at least one second pulse sequence are applied in a first logging passe and a second logging pass respectively, the second logging pass occurring subsequent to the first logging pass, the method further comprising:
    (i) determining an absolute difference between the first and second summation signal at the at least one depth; and
    (ii) flagging for further review the first and second echo trains if said absolute difference is greater than a predetermined value.

19. The method of claim 18 wherein the at least one depth further comprises a plurality of depths, the method further comprising determining a sum of said absolute differences over the plurality of depths and flagging for further review the first and second echo trains if said absolute difference is greater than a predetermined value.

20. The method of claim 18 wherein the second summation signal is determined during the second logging pass.

21. A method of determining a parameter of interest of a volume of earth formation in a reservoir adjacent a borehole, said parameter of interest including at least one of a longitudinal relaxation time $T_1$ and a transverse relaxation time $T_2$ of a fluid in the reservoir, the method comprising:
  (a) using a magnet assembly on a borehole tool conveyed in the borehole at a plurality of depths for producing a static magnetic field in said volume of the formation thereby aligning nuclear spins within said volume parallel to a direction of the static field;
  (b) producing a radio frequency (RF) magnetic field in said volume of the formation with an antenna on the borehole tool, said RF magnetic field having a direction orthogonal to a direction of the static field, the RF field including a phase alternated pulse sequence $TW_A$–$90_{\pm X}$–(t–X–t–echo)$_j$ to produce an in-phase echo train and a quadrature echo train,
    wherein 90 is a tipping pulse for tipping the nuclear spins at an angle substantially equal to ninety degrees to cause precession thereof, $TW_A$ is a wait time, X is a refocusing pulse, and j=1, 2, ... J, where J is the number of echoes collected in a single sequence of pulses;
  (c) at each of said plurality of depths, correcting at least one of said in-phase and quadrature echo trains for ringing and DC offset;
  (d) at each of said plurality of depths, determining a sum of the at least one of the corrected in-phase echo train and the corrected quadrature echo train;
  (e) comparing fluctuations at said plurality of depths of a normalized value of the sum of the at least one of the corrected in-phase and quadrature echo trains with a fluctuations of a magnitude of the j-th echo, where $2 \leq j \leq 4$;
  (f) discarding as unacceptable echo train data from those of said plurality of depths where the fluctuations of said normalized value of the sum of the at least one of the corrected in-phase and quadrature echo trains exceed fluctuations of the magnitude of said j-th echo; and
  (g) determining said parameter of interest from at least a portion of the remaining echo train data.

22. A method of determining a parameter of interest at a plurality of depths of a volume of earth formation in a reservoir adjacent a borehole, said parameter of interest expected to be substantially constant at said plurality of depths, said parameter of interest including at least one of a longitudinal relaxation time $T_1$ and a transverse relaxation time $T_2$ of a fluid in the reservoir, the method comprising:
  (a) using a magnet assembly on a borehole tool conveyed in the borehole at said plurality of depths for producing a static magnetic field in said volume of the formation thereby aligning nuclear spins within said volume parallel to a direction of the static field;
  (b) producing a radio frequency (RF) magnetic field in said volume of the formation with an antenna on the borehole tool, said RF magnetic field having a direction orthogonal to a direction of the static field, the RF field including a phase alternated pulse sequence $TW_A$–$90_{\pm X}$–(t–X–t–echo)$_j$ to produce an in-phase echo train and a quadrature echo train,
    wherein 90 is a tipping pulse for tipping the nuclear spins at an angle substantially equal to ninety degrees to cause precession thereof, $TW_A$ is a wait time, X is a refocusing pulse, and j=1, 2, ... J, where J is the number of echoes collected in a single sequence of pulses;
  (c) at each of said plurality of depths, correcting at least one of said in-phase and quadrature echo trains for ringing and DC offset;
  (d) at each of said plurality of depths, determining a sum of the at least one corrected echo train, giving at least one summed component;
  (e) rejecting those echo trains for which the at least one summed component has a value less than a predetermined threshold and
  (f) determining said parameter of interest from at least a portion of the remaining echo trains.

23. The method of claim 22 wherein the predetermined value is based upon a cross plot of the least one summed component signal and porosity.

* * * * *